United States Patent
Rempfler

[11] Patent Number: 5,312,800
[45] Date of Patent: May 17, 1994

[54] PYRROLIDINONES

[75] Inventor: Hermann Rempfler, Ettingen, Switzerland

[73] Assignee: Ciba-Geigy Corporation, Ardsley, N.Y.

[21] Appl. No.: 64,243

[22] Filed: May 20, 1993

[30] Foreign Application Priority Data

May 22, 1992 [CH] Switzerland .................. 1655/92

[51] Int. Cl.$^5$ .................. A01N 43/36; A01N 43/08; C07D 405/10
[52] U.S. Cl. .................. 504/283; 504/287; 548/526
[58] Field of Search .................. 548/526; 504/283, 287

[56] References Cited

U.S. PATENT DOCUMENTS

| | | | |
|---|---|---|---|
| 4,110,105 | 8/1978 | Teach | 71/95 |
| 4,132,713 | 1/1979 | Broadhurst | 260/326.5 FL |
| 4,210,589 | 7/1980 | Teach | 260/326.5 |
| 4,645,843 | 1/1987 | Broadhurst et al. | 548/543 |
| 4,722,935 | 2/1988 | Ehrenfreund | 514/465 |
| 4,859,783 | 8/1989 | Ehrenfreund | 549/439 |
| 4,874,422 | 10/1989 | Woolard | 71/95 |
| 4,956,006 | 9/1990 | Woolard | 71/95 |
| 4,960,457 | 10/1990 | Woolard | 71/95 |

FOREIGN PATENT DOCUMENTS

| | | | |
|---|---|---|---|
| 1163640 | 3/1984 | Canada | 548/526 |
| 0055215 | 6/1982 | European Pat. Off. | 548/526 |
| 0134564 | 3/1985 | European Pat. Off. | 548/526 |
| 0198797 | 10/1986 | European Pat. Off. | 549/439 |
| 0387869 | 9/1990 | European Pat. Off. | 548/526 |

OTHER PUBLICATIONS

Chemical Abstracts, vol. 97, (1982), 97:182204c, Rempfler et al.

Primary Examiner—Mary C. Lee
Assistant Examiner—Joseph K. McKane
Attorney, Agent, or Firm—Edward McC. Roberts

[57] ABSTRACT

Pyrrolidinones of formula I

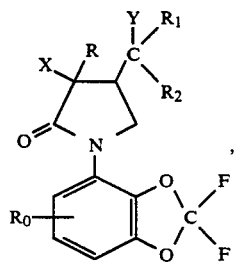

wherein
R is hydrogen, $C_1$-$C_4$alkyl, or phenyl unsubstituted or substituted by halogen, $C_1$-$C_4$alkyl or by $C_1$-$C_4$haloalkyl, or is fluorine, chlorine or bromine;
$R_0$ is hydrogen or halogen;
$R_1$ and $R_2$ independently of one another are hydrogen or $C_1$-$C_4$alkyl;
X is hydrogen, flourine, chlorine, bromine, cyano, —COOR$_1$, —CONR$_1$R$_2$, —NH$_2$ or —NHCOR$_3$, wherein $R_1$ and $R_2$ are as defined, and $R_3$ is $C_1$-$C_4$alkyl; and
Y is hydrogen, chlorine or bromine; and the diastereoisomeric forms thereof, exhibit pre- and post-emergence herbicidal properties. The preparation of those compounds and their use as herbicidal active ingredients are described.

14 Claims, No Drawings

PYRROLIDINONES

The present invention relates to novel herbicidally active pyrrolidinones, to processes for the preparation thereof, to compositions comprising those pyrrolidinones as active ingredients, and to the use thereof in controlling weeds, especially in crops of useful plants, such as cereals, rice, maize, soybeans and cotton.

N-substituted pyrrolidinones having herbicidal activity are already known and are described, for example, in U.S. Pat. No. 4,874,422, 4,956,006, 4,960,457 and EP-A-0 055 215.

Novel pyrrolidinones having herbicidal properties that are distinguished by good activity have now been found.

The pyrrolidinones according to the invention correspond to formula I

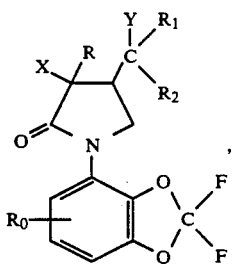
(I)

wherein
R is hydrogen, $C_1$–$C_4$alkyl, or phenyl unsubstituted or substituted by halogen, $C_1$–$C_4$alkyl or by $C_1$–$C_4$-haloalkyl, or is fluorine, chlorine or bromine;
$R_0$ is hydrogen or halogen;
$R_1$ and $R_2$ independently of one another are hydrogen or $C_1$–$C_4$alkyl;
X is hydrogen, fluorine, chlorine, bromine, cyano, —$COOR_1$, —$CONR_1R_2$, —$NH_2$ or —$NHCOR_3$, wherein $R_1$ and $R_2$ are as defined, and $R_3$ is $C_1$–$C_4$alkyl; and
Y is hydrogen, chlorine or bromine; and the diastereoisomeric forms thereof.

In the above definitions, halogen is to be understood as being iodine and preferably fluorine, chlorine and bromine.

Suitable alkyl groups are straight-chained or branched alkyl groups, for example methyl, ethyl, n-propyl, isopropyl, n-butyl, sec-butyl, isobutyl and tert-butyl; preferably methyl and ethyl.

Suitable as haloalkyl are alkyl groups mono- or poly-substituted, especially mono- to tri-substituted, by halogen, halogen being bromine or iodine and especially fluorine or chlorine, for example fluoromethyl, difluoromethyl, chloromethyl, dichloromethyl, trichloromethyl and especially trifluoromethyl.

The pyrrolidinones of formula I according to the invention have good selectivity in crops of useful plants such as cereals, rice, maize, soybeans and cotton when applied post-emergence, but especially when applied pre-emergence.

Preference is given to the compounds of formula $I_a$

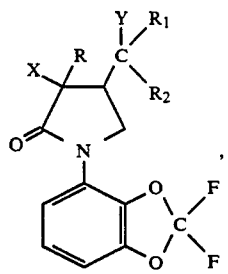
($I_a$)

wherein R, $R_1$, $R_2$, X and Y are as defined above. Of those compounds of formula $I_a$, special preference is given to those wherein the radical
R is hydrogen, methyl, fluorine, chlorine, phenyl, 3-chlorophenyl or 3-fluorophenyl;
$R_1$ and $R_2$ independently of one another are hydrogen, methyl or ethyl; and
X is hydrogen, fluorine, chlorine or bromine.

Very special preference is given to those compounds of formula $I_a$, including all the preferences mentioned, wherein
R is hydrogen or phenyl;
$R_1$ and $R_2$ independently of one another are hydrogen or methyl;
X is hydrogen, fluorine or chlorine; and
Y is hydrogen or chlorine.

Preference is given also to compounds of formula $I_b$

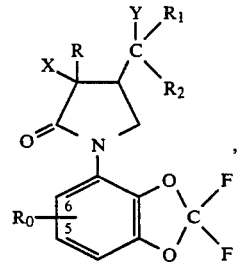
($I_b$)

wherein
$R_0$ is bonded in the 5- or 6-position and is halogen, especially chlorine or bromine;
R is hydrogen, methyl or ethyl;
$R_1$ and $R_2$ independently of one another are hydrogen or methyl;
X is fluorine or chlorine; and
Y is hydrogen or chlorine.

Of especial importance are compounds of formula I wherein
R is hydrogen, fluorine, chlorine, methyl, ethyl, phenyl, 3-chlorophenyl or 3-fluorophenyl;
$R_0$ is hydrogen, 5- or 6-chlorine, or 5-bromine;
$R_1$ and $R_2$ independently of one another are hydrogen, methyl or ethyl; and
X is hydrogen, fluorine, chlorine or bromine.

Of those compounds of formula I, very especial importance is accorded to those wherein
R is hydrogen, fluorine, chlorine, methyl or phenyl;
$R_0$ is hydrogen; and
$R_1$ and $R_2$ independently of one another are hydrogen or methyl.

Preferred individual compounds of formula I that may be mentioned are:

N-[(2,3-difluoromethylenedioxy)-phenyl]-3-chloro-4-chloromethylpyrrolidin-2-one;

N-[(2,3-difluoromethylenedioxy)-phenyl]-3-fluoro-4-ethylpyrrolidin-2-one;

N-[(2,3-difluoromethylenedioxy)-phenyl]-3,3-dichloro-4-chloromethylpyrrolidin-2-one;

N-[(2,3-difluoromethylenedioxy)-phenyl]-3-bromo-4-ethylpyrrolidin-2-one; and

N-[(2,3-difluoromethylenedioxy)-phenyl]-3,3-difluoro-4-ethylpyrrolidin-2-one.

The process according to the invention for the preparation of the compounds of formula I is effected analogously to known processes and comprises:

a) for the preparation of the pyrrolidinone derivatives of formula $I_c$

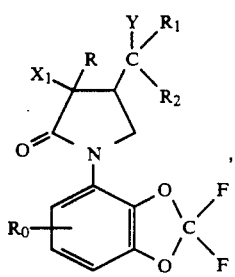

wherein R, $R_0$, $R_1$, $R_2$ and Y are as defined, and $X_1$ is hydrogen, fluorine, chlorine or bromine, cyclising a compound of formula II

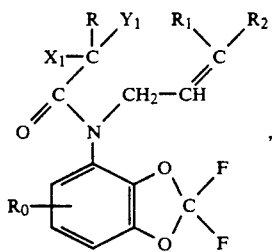

wherein R, $R_0$, $R_1$, $R_2$ and $X_1$ are as defined, and $Y_1$ is chlorine or bromine, in an inert organic solvent in the presence of a catalyst;

b) for the preparation of the pyrrolidinone derivatives of formula $I_e$

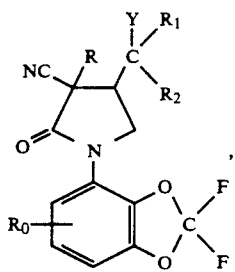

wherein R, $R_0$, $R_1$, $R_2$ and Y are as defined, reacting a compound of formula $I_f$

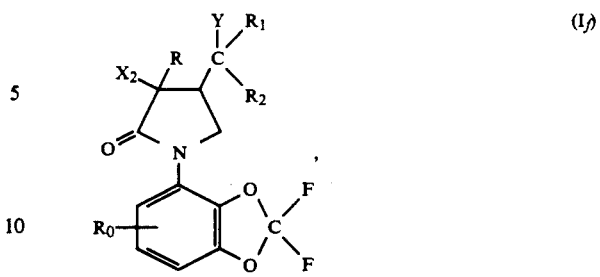

wherein R, $R_0$, $R_1$, $R_2$ and Y are as defined, and $X_2$ is chlorine or bromine, with a metal cyanide of formula VII $$M^{\oplus}CN^{\ominus} \qquad (VII),$$

wherein $M^{\oplus}$ is an alkali metal ion, especially sodium or potassium;

c) for the preparation of the pyrrolidinone derivatives of formula $I_g$

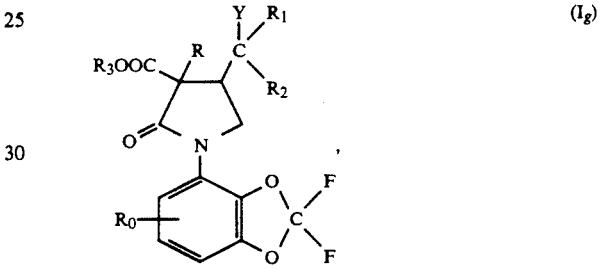

wherein R, $R_0$, $R_1$, $R_2$, $R_3$ and Y are as defined, hydrolysing a compound of formula $I_e$

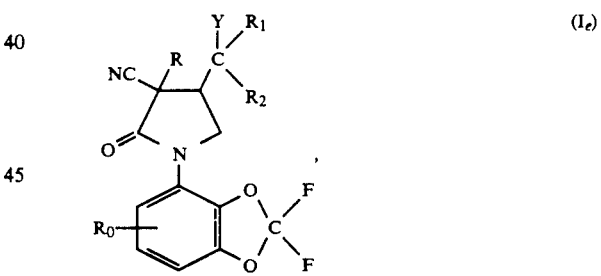

wherein R, $R_0$, $R_1$, $R_2$ and Y are as defined, under acididic or, especially, basic conditions to form a carboxylic acid of formula $I_h$

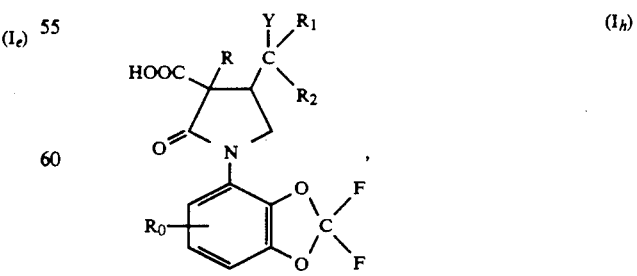

wherein R, $R_0$, $R_1$, $R_2$ and Y are as defined, and then reacting the latter with an alcohol of formula VIII

R$_3$OH  (VIII), wherein R$_3$ is C$_1$-C$_4$alkyl;

c$_1$) for the preparation of the pyrrolidinone derivatives of formula I$_g$, the carboxylic acids of formula I$_h$ may preferably also be converted into the corresponding acid chlorides of formula I$_o$

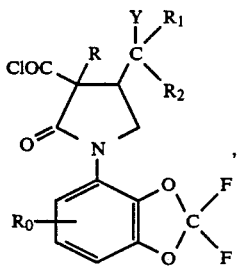

which are then reacted with the alcohol of formula VIII;

d) for the preparation of the pyrrolidinone derivatives of formula I$_d$

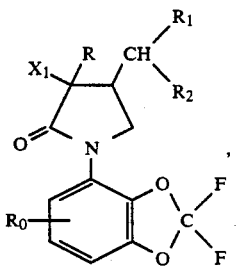

wherein R, R$_0$, R$_1$, R$_2$ and X$_1$ are as defined, cyclising reductively a compound of formula II

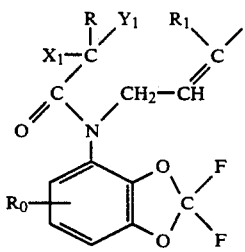

wherein R, R$_0$, R$_1$, R$_2$, X$_1$ and Y$_1$ are as defined, in an inert organic solvent in the presence of a reducing agent and a radical-initiator;

e) for the preparation of the pyrrolidinone derivatives of formula I$_i$

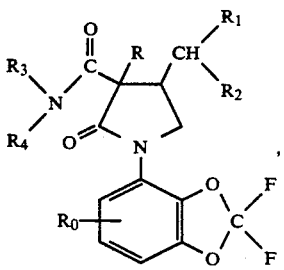

wherein R, R$_0$, R$_1$, R$_2$ and R$_3$ are as defined, and R$_4$ is hydrogen or C$_1$-C$_4$alkyl, reacting a compound of formula I$_j$

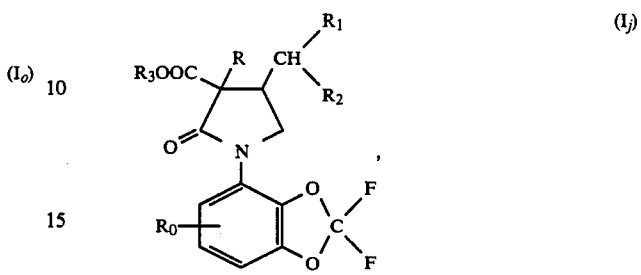

wherein R, R$_0$, R$_1$, R$_2$ and R$_3$ are as defined, with the aid of an acid or base catalyst, with a compound of formula IX

R$_3$R$_4$NH  (IX), wherein R$_3$ and R$_4$ are as defined above.

The N-substituted or N,N-disubstituted amides of formula I$_i$ can preferably be prepared analogously to process variant c$_1$) from the carboxylic acids of formula I$_m$

via the corresponding acid chlorides of formula I$_p$

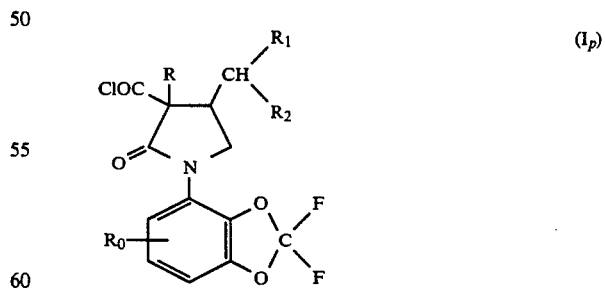

in accordance with process variant c$_1$), by reacting the acid chlorides of formula I$_p$ with the amine of formula IX; and f) for the preparation of the pyrrolidinone derivatives of formula I$_k$

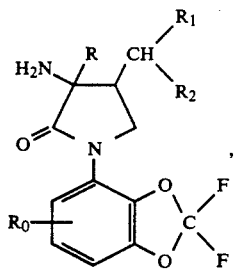
wherein R, $R_0$, $R_1$ and $R_2$ are as defined, reacting a compound of formula $I_n$
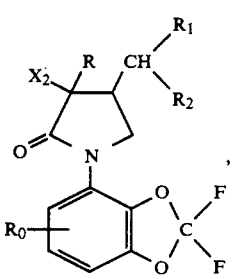
wherein R, $R_0$, $R_1$ and $R_2$ are as defined, and $X_2$ is chlorine or bromine, with ammonia.
Process variants a), b), c) and $c_1$) follow reaction scheme 1 and process variants d), e) and f) follow reaction scheme 2.
Reaction scheme 1:
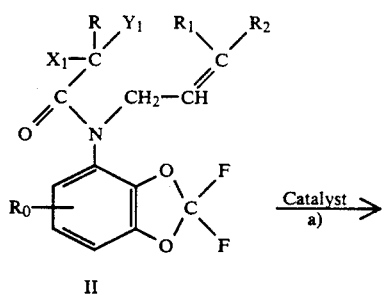
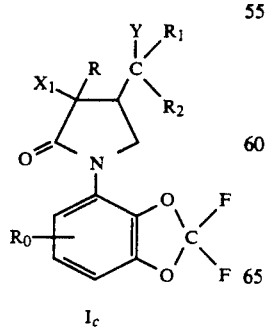
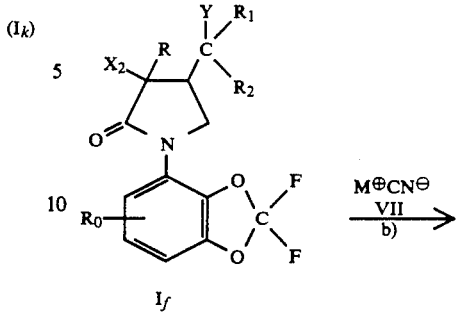
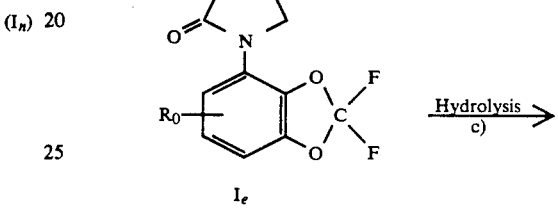
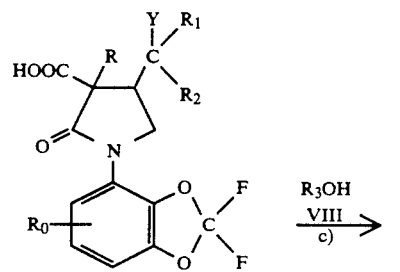
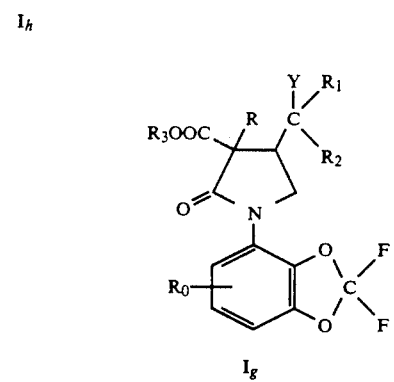
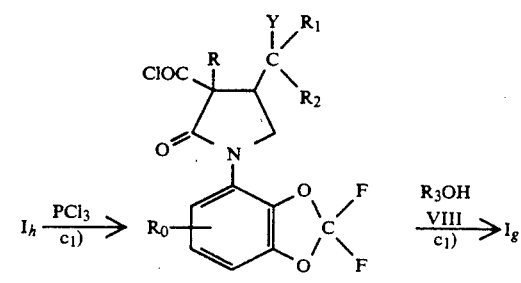
Reaction scheme 2:

-continued
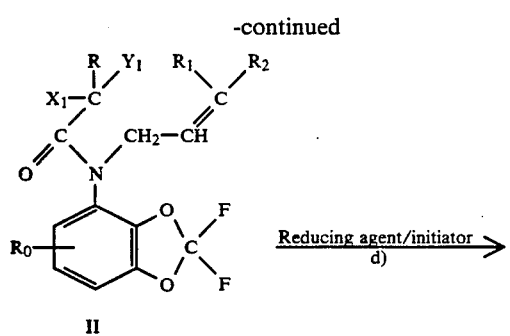
Reducing agent/initiator
d)
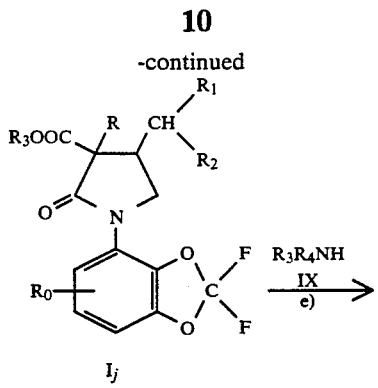
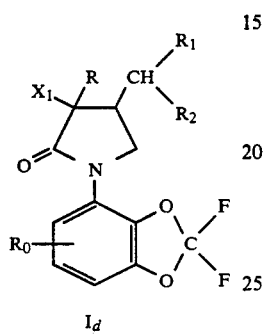
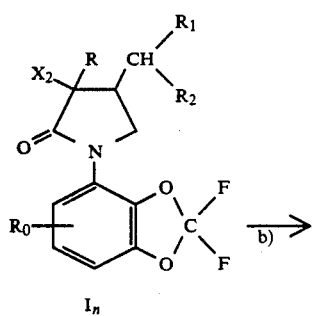
b)
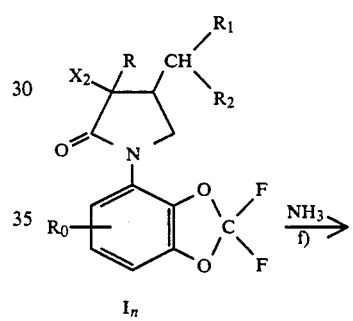
$\xrightarrow[f)]{NH_3}$
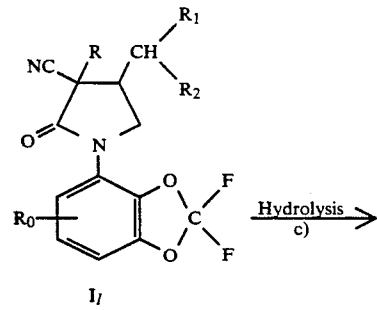
Hydrolysis
c)
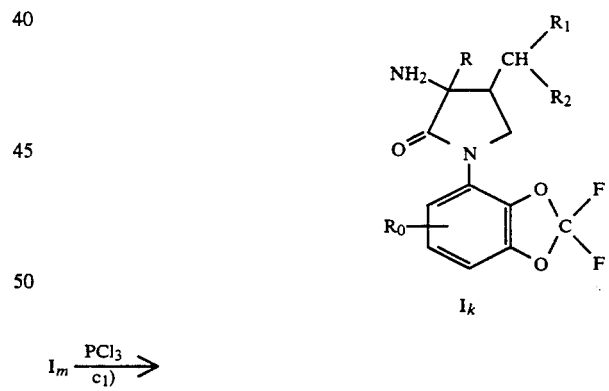
$I_m \xrightarrow[c_1)]{PCl_3}$
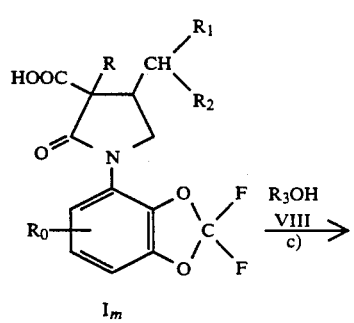
$\xrightarrow[c)]{R_3OH \atop VIII}$
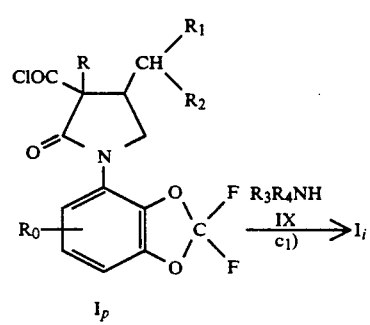
$\xrightarrow[c_1)]{R_3R_4NH \atop IX} I_i$ The pyrrolidinone derivatives of formulae $I_i$ and $I_j$ in reaction scheme 2 are analogues of the compounds of formulae $I_e$ (Y=H) and $I_g$ (Y=H) in reaction scheme 1, and are obtainable analogously to process variants b) and c).

In the ring-closure reaction ($II—I_c/II—I_d$), the two possible configuration isomers of the compounds of formula I according to the invention: the Z-isomer and the E-isomer may be formed. In general, an isomeric mixture is formed, which can be separated into its components by suitable working-up methods, such as fractional crystallisation, distillation, chromatography or extraction. Unless mentioned specifically below, a compound of formula I is always to be understood as being an isomeric mixture.

The cyclisation according to process variant a) can advantageously be carried out by treating the compound of formula II in an inert aprotic organic solvent, such as an aliphatic or alicyclic ether, for example diethylene glycol dimethyl ether, with a base at temperatures of from 80° C. to 200° C. in the presence of a catalyst, preferably at temperatures of from 120° C. to 160° C. Examples of suitable catalysts are copper(I) chloride, copper(I) bromide and iron(III) chloride. Examples of suitable bases are aliphatic or alicyclic amines, preferably 2,2'-bipyridyl, piperidine or diethylamine in combination with copper(I) chloride.

In process variant d), the expression "cyclised reductively" stands for the introduction of hydrogen as the substituent $Y_1$ in compound II with simultaneous ring-closure. Suitable reducing agents are advantageously alkyl- or aryl-tin hydrides such as $C_1$-$C_5$trialkyl- or triphenyl-tin hydride in aprotic organic solvents at temperatures of from 20° C. to 200° C., preferably from 50° C. to 150° C. 2,2'-Azaisobutyric acid dinitrile (AIBN) is preferably used as radical-initiator.

In the cyanide addition reaction according to process variant b), a halogen substituent ($X_2$ is chlorine or bromine) is replaced by a cyano group by means of a metal cyanide of formula VII. The latter is especially an alkali metal cyanide, especially sodium or potassium cyanide. The replacement reaction is advantageously effected in the presence of an aprotic polar solvent, for example a dialkyl sulfoxide, such as dimethyl sulfoxide, or a dialkylamide, such as dimethylformamide, or an alkylnitrile, such as aceto- or butyronitrile, at temperatures of from 40° C. to 180° C., preferably from 80° C. to 160° C. By the addition of suitable crown ethers the reaction temperature can generally be kept even lower, for example at from 20° C. to 80° C.

The hydrolysis of the compounds of formula $I_e$ in accordance with process variant c) is advantageously carried out in an acidic or, preferably, basic aqueous solution, for example in aqueous sodium hydroxide solution. The reaction is carried out at temperatures of from 0° C. to 120° C. The subsequent esterification of the resulting carboxylic acids of formula $I_h$ with the alcohol of formula VIII is effected in accordance with the customary base-catalysed or especially acid-catalysed processes, by 1) adding the alcohol of formula VIII in excess as solvent, or by 2) removing the water of reaction that forms by means of distillation or molecular sieve, or by 3) using agents for removing the elements of water, for example dicyclohexylcarbodiimide or trifluoroacetic acid anhydride. Suitable acid catalysts are especially sulfuric acid or p-toluenesulfonic acid. Preferably, the esters of formulae $I_g$ and $I_j$ can also be prepared in accordance with process variant $c_1$) by converting the corresponding carboxylic acid of formula $I_h$ or $I_m$, respectively, in customary manner with phosphorus trichloride, phosphorus pentachloride, phosphorus oxychloride or thionyl chloride into the corresponding acid chloride of formula $I_o$ or $I_p$, respectively, and then reacting the latter with the alcohol of formula VIII, especially with the aid of a base catalyst.

In the preparation of the N-substituted or N,N-disubstituted amides of formula $I_i$ in accordance with process variant e), the ester of formula $I_j$ is advantageously reacted with the corresponding amine of formula IX in the presence of a base or of an acid, preferably in an excess of the corresponding amine of formula IX, at temperatures of from 0° C. to the boiling temperature of the reaction mixture, preferably from 20° C. to 150° C.

The N-substituted or N,N-disubstituted amides of formula $I_i$ can preferably also be prepared analogously to process variant $c_1$) by converting the corresponding carboxylic acid of formula $I_m$ according to process variant $c_1$) into the corresponding acid chloride of formula $I_p$ and then reacting the latter, with the aid of a base catalyst, with the amine of formula IX.

In the preparation of the amine of formula $I_k$ in accordance with process variant f), the compound of formula $I_n$ is reacted with an excess of ammonia with or without a solvent, preferably in a closed pressure vessel, at temperatures of from 0° C. to 150° C.

The compounds of formulae $I_c$, $I_d$, $I_e$, $I_f$, $I_g$, $I_i$, $I_j$, $I_k$, $I_l$, $I_m$ and $I_n$ can be isolated and purified in accordance with methods known per se. In addition, the person skilled in the art will be familiar with the sequence in which certain reactions in process variants a) to f) are advantageously carried out in order where possible to avoid secondary reactions.

Where the synthesis is not specifically targeted at the isolation of pure isomers, the product may be obtained in the form of a mixture of two or more isomers. The isomers can be separated in accordance with methods known per se.

The novel intermediates of formula II can be prepared in accordance with various standard methods known from the literature, for example in accordance with reaction scheme 3 which follows:

Reaction scheme 3:

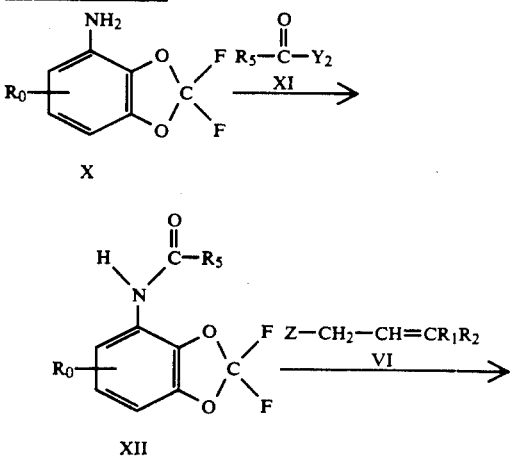

Reaction scheme 3:

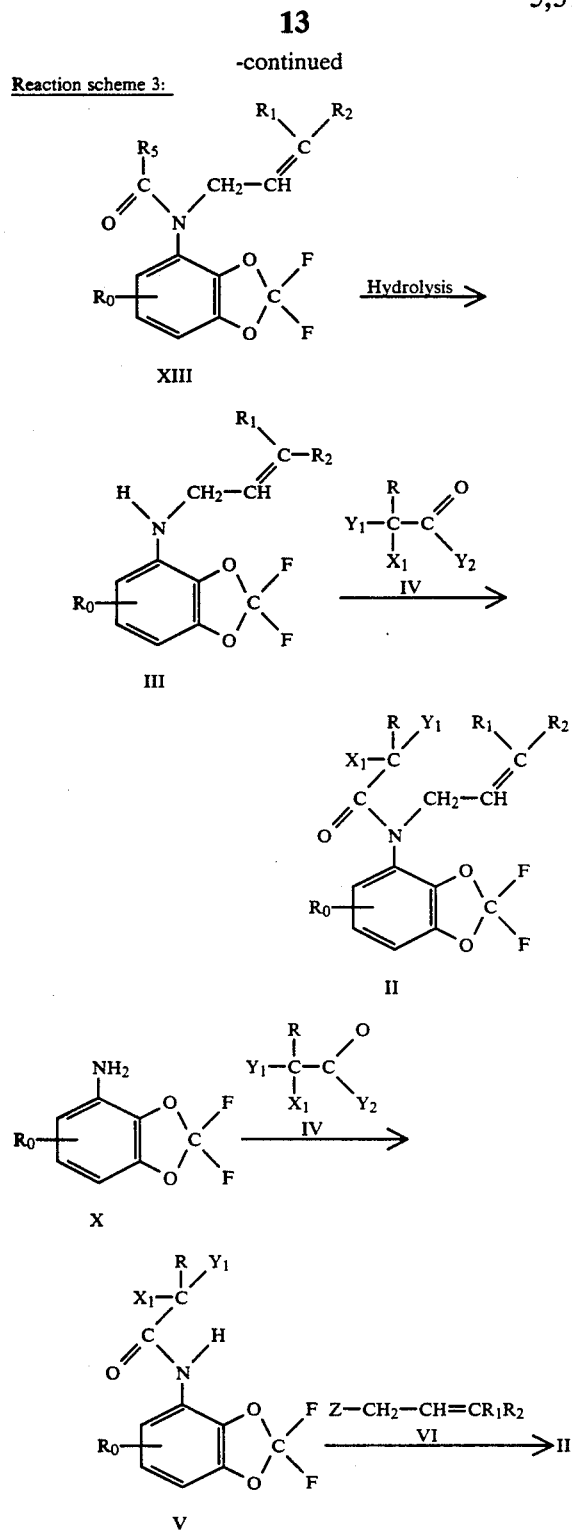

In accordance with that reaction scheme, a compound of formula II is obtained by reacting an aniline derivative of formula X, wherein $R_0$ is as defined, with reactive acid derivative of formula XI wherein $R_5$ is $C_1$-$C_4$alkyl and $Y_2$ is a leaving group, for example halogen, especially chlorine, or an acyloxy group, for example —O—C(O)—$R_5$, in the presence of a suitable base, for example triethylamine, to form a compound of formula XII, preferably in a temperature range of from −10° C. to +50° C. Suitable solvents are aliphatic or cyclic ethers, for example 1,2-dimethoxyethane, tetrahydrofuran or dioxane; toluene; or chlorinated hydrocarbons.

The acylated aniline derivatives of formula XII are then reacted with the compound of formula VI wherein $R_1$ and $R_2$ are as defined and Z is chlorine, bromine or iodine, in inert organic solvents, for example ketones such as acetone or methyl ethyl ketone; dimethylformamide; or dimethyl sulfoxide, in the presence of an inorganic or organic base, such as sodium carbonate or triethylamine, in a temperature range of from 20° C. to 150° C. to form the compounds of formula XIII.

The acyl-protecting group in the resulting compound of formula XIII is removed hydrolytically, preferably in the presence of an aqueous acid, at temperatures of from 20° C. to 100° C. Suitable acids are especially sulfuric acid and hydrochloric acid. In the final reaction step, the acylation of the resulting allyl aniline of formula III with the compound of formula IV wherein R, $X_1$, Y and $Y_2$ are as defined above leads to the desired intermediate of formula II.

The intermediate of formula II can also be obtained in analogous manner starting from the aniline derivative of formula X, via the intermediate of formula V

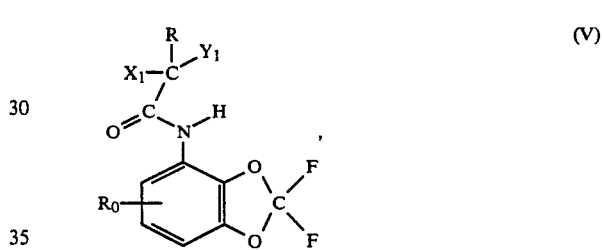

wherein R, $R_0$, $X_1$ and $Y_1$ are as defined above, and subsequent reaction with the reagent of formula VI.

The intermediates of formulae II, III and V are novel and have been developed specifically for the synthesis of compounds of formula I. The present invention therefore relates also to those intermediates.

The same preferences apply in the case of the intermediates of formulae II, III and V as in the case of the compounds of formula I.

The starting compounds of formula X required for the preparation processes can be prepared in accordance with various processes known from the literature, for example for compounds of formula $X_a$ ($R_0$=5-Cl) or for compounds of formula $X_b$ ($R_0$=6-Cl) in accordance with reaction scheme 4 which follows:

Reaction scheme 4:

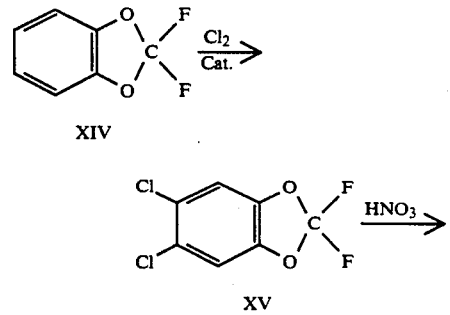

Reaction scheme 4:
-continued

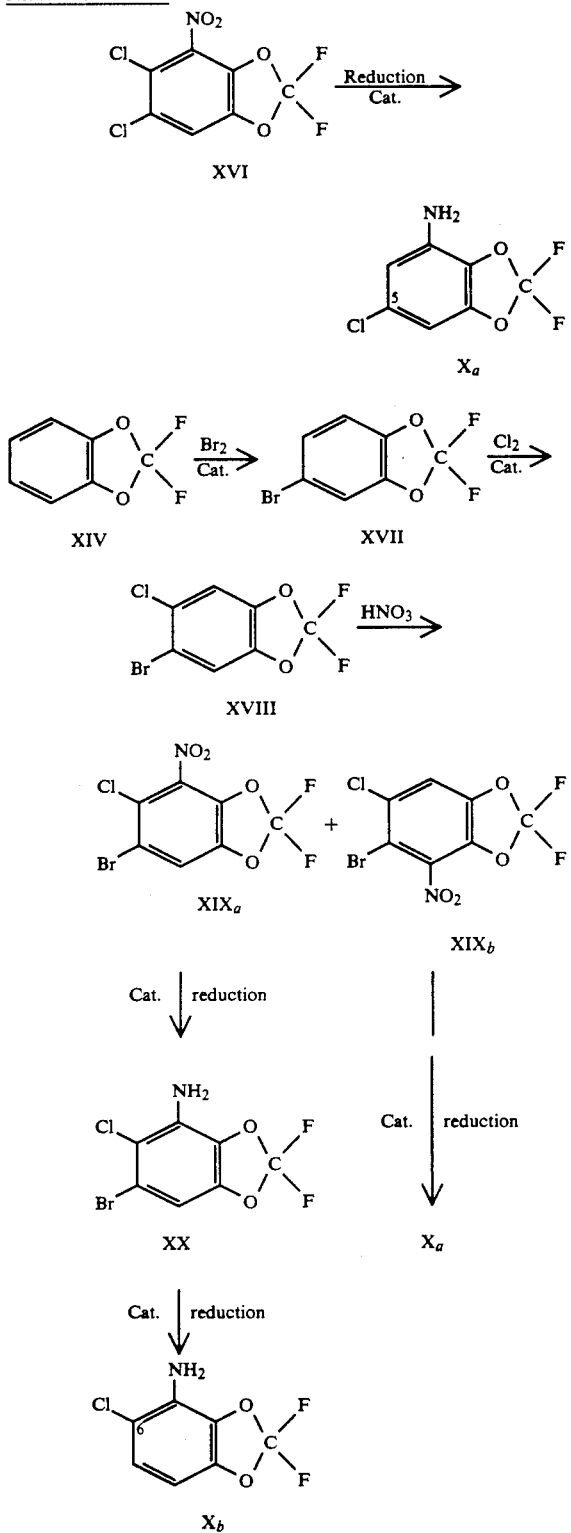

In accordance with that reaction scheme, the 5-chloroaniline derivative of formula $X_a$ is obtained by chlorinating the compound of formula XIV, with or without a solvent in the presence of a catalyst. Suitable catalysts are Lewis acids, especially iron(III) chloride and copper(II) chloride. Suitable solvents are chlorinated hydrocarbons, such as carbon tetrachloride. The subsequent nitration with concentrated nitric acid results in the product of formula XVI and the catalytic reduction results finally in the desired 5-chloroaniline derivative of formula $X_a$.

The 6-chloroaniline derivative of formula $X_b$ is obtained by means of catalytic bromination from the compound of formula XIV, subsequent catalytic chlorination of the intermediate of formula XVII and nitration of the 4-bromo-5-chlorobenzene of formula XVIII via the separated isomeric dihalonitrobenzene of formula $XIX_a$, and subsequent catalytic reduction which is carried out twice. The 5-chloroaniline derivative of formula $X_a$ can also be obtained from the separated isomeric dihalonitrobenzene of formula $XIX_b$ by means of catalytic reduction.

The preparation of the required starting compound of formula $X_c$

is described in EP-A-0 198 797. The starting compound of formula XIV is a customary, commercially available intermediate.

The compounds of formula I are used in unmodified form, as obtainable from synthesis, or, preferably, together with the adjuvants conventionally employed in formulation technology, and are therefore formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures comprising the compound (active ingredient) of formula I and, where appropriate, one or more solid or liquid adjuvants, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloaliphatic hydrocarbons such as paraffins, cyclohexane or tetrahydronaphthalene; alcohols such as ethanol, propanol or butanol; glycols and their ethers and esters, such as propylene glycol or dipropylene glycol ether, ketones such as cyclohexanone, isophorone or diacetone alcohol, strongly polar solvents such as N-methyl-2-pyrrolidone, dimethyl sulfoxide or water; vegetable oils and their esters, such as rape oil, castor oil or soybean oil; and, where appropriate, also silicone oils.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty alcohol sulfonates, fatty alcohol sulfates, sulfonated benzimidazole derivatives or alkylaryl-sulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprises the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology that may also be used in the formulations according to the invention are described inter alia in the following publications:

"Mc Cutcheon's Detergents and Emulsifiers Annual", Mc Publishing Corp., Glen Rock, N.J., 1988.

M. and J. Ash, "Encyclopedia of Surfactants", Vol. I-III, Chemical Publishing Co., New York, 1980–1981.

Dr. Helmut Stache "Tensid-Taschenbuch", Carl Hanser Verlag, Munich/Vienna 1981.

The herbicidal compositions generally comprise 0.1 to 99%, preferably 0.1 to 95%, of a compound of formula I, 1 to 99% of a solid or liquid adjuvant and 0 to 25%, preferably 0.1 to 25%, of a surfactant.

Whereas commercial products will preferably be formulated as concentrates, the end user will normally employ dilute formulations.

The compositions may also comprise further additives such as stabilisers, for example vegetable oils and epoxidised vegetable oils (epoxidised coconut oil, rape oil or soybean oil), antifoams, for example silicone oil, preservatives, viscosity regulators, binders and tackifiers, as well as fertilisers or other active ingredients for obtaining special effects.

Preferred formulations have especially the following composition (throughout, percentages are by weight):

| Emulsifiable concentrates: | |
| --- | --- |
| active ingredient: | 1 to 90%, preferably 5 to 50% |
| surface-active agent: | 5 to 30%, preferably 10 to 20% |
| liquid carrier: | 15 to 94%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.5 to 30%, preferably 3 to 15% |
| solid carrier: | 99.5 to 70%, preferably 97 to 85% |

The following Examples further illustrate the invention, without limiting it.

1. PREPARATION EXAMPLES

Example P1

N-[(2,3-difluoromethylenedioxy)-phenyl]-3-chloro-4-chloromethylpyrrolidin-2-one

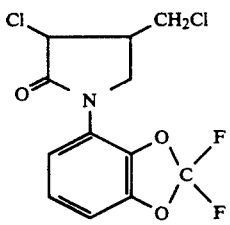
(1.001)

84.0 g (0.259 mol) of N-allyl-N-dichloroacetyl-2,3-difluoromethylenedioxyaniline are added dropwise at 130°–140° C. to 3.7 g (0.037 mol) of copper(I) chloride and 5.5 g (0.035 mol) of 2,2'-bipyridyl in 400 ml of dry diethylene glycol dimethyl ether. When the slightly exothermic reaction has subsided, the reaction mixture is stirred for ¼ hour at 140° C. and then cooled and poured into water. The mixture is extracted by shaking with ethyl acetate and the ethyl acetate phase is washed three times with water and once with brine, and then dried over sodium sulfate and concentrated by evaporation. The oily residue is filtered through a silica gel column with ethyl acetate/hexane 1:4, concentrated by evaporation and dried under a high vacuum. Trituration in hexane causes the product to crystallise in the form of a diastereoisomeric mixture. 67.0 g of N-[(2,3-difluoromethylenedioxy)-phenyl]-3-chloro-4-chloromethylpyrrolidin-2-one having a melting point of 68°–71° C. are obtained.

EXAMPLE P2

N-Allyl-N-dichloroacetyl-2,3-difluoromethylenedioxyaniline (intermediate)

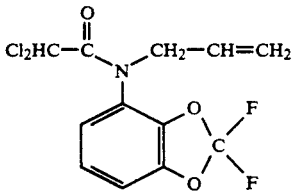

37 g (0.30 mol) of allyl bromide are added dropwise at 30° C. to 71 g (0.25 mol) of N-dichloroacetyl-2,3-difluoromethylenedioxyaniline and 39 g (0.28 mol) of potassium carbonate in 500 ml of dimethyl sulfoxide. When the exothermic reaction has subsided, the mixture is stirred at room temperature overnight. The reaction mixture is poured onto ice-water and extracted by shaking with ethyl acetate. The ethyl acetate phase is washed once with water and once with brine, dried over sodium sulfate and concentrated by evaporation to yield 75.5 g of the desired N-allyl-N-dichloroacetyl-2,3-difluoromethylenedioxyaniline in the form of a yellow oil which is used directly in the following step.

That intermediate can also be prepared from N-allyl-2,3-difluoromethylenedioxyaniline and dichloroacetyl chloride in diethyl ether in the presence of a base, such as triethylamine, analogously to Example 1a) of EP-A-0 055 215, or in dimethyl sulfoxide, or in ethyl methyl ketone or N,N-dimethylformamide in the presence of potassium carbonate.

EXAMPLE P3:

N-Dichloroacetyl-2,3-difluoromethylenedioxyaniline (intermediate)

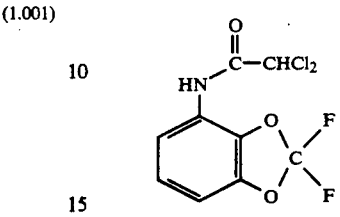

48.6 g (0.33 mol) of dichloroacetyl chloride are added dropwise in the course of two hours, at from 0° to 5° C., to 52.0 g (0.30 mol) of 2,3-difluoromethylenedioxyaniline and 36.0 g (0.36 mol) of triethylamine in 800 ml of diethyl ether. After stirring for one hour, the salt is filtered off, the filtrate is washed with water and dried over sodium sulfate and the ether is evaporated. Trituration in hexane yields white crystals, which are filtered off to yield 68.0 g of the desired N-dichloroacetyl-2,3-difluoromethylenedioxyaniline having a melting point of 103°–104° C.

The compounds of formulae Ia, Ib and II listed in the following Tables 1, 2 and 3 are prepared analogously.

TABLE 1

Compounds of formula Ia

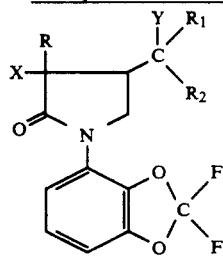
(Ia)

| Comp. No. | X | Y | R | $R_1$ | $R_2$ | phys.-chem. data |
|---|---|---|---|---|---|---|
| 1.001 | Cl | Cl | H | H | H | m.p. 68–71° C. |
| 1.002 | Cl | Cl | H | $CH_3$ | H | m.p. 70–78° C. |
| 1.003 | Cl | H | H | $CH_3$ | H | |
| 1.004 | F | Cl | H | H | H | $n_D^{26}$ 1.5032 |
| 1.005 | F | Cl | H | $CH_3$ | H | $n_D^{40}$ 1.5053 |
| 1.006 | F | H | H | $CH_3$ | H | $n_D^{25}$ 1.5032 |
| 1.007 | Cl | Cl | H | $CH_3$ | $CH_3$ | m.p. 108–112° C. |
| 1.008 | Cl | H | H | $CH_3$ | $CH_3$ | $n_D^{22}$ 1.5102 |
| 1.009 | F | Cl | H | $CH_3$ | $CH_3$ | $n_D^{25}$ 1.5140 |
| 1.010 | F | H | H | $CH_3$ | $CH_3$ | $n_D^{25}$ 1.4970 |
| 1.011 | Cl | Cl | Cl | H | H | $n_D^{25}$ 1.5373 |
| 1.012 | Cl | Cl | Cl | $CH_3$ | H | |
| 1.013 | Cl | H | Cl | $CH_3$ | H | |
| 1.014 | F | Cl | Cl | H | H | |
| 1.015 | F | H | Cl | H | H | |
| 1.016 | F | Cl | Cl | $CH_3$ | H | |
| 1.017 | F | H | Cl | $CH_3$ | H | |
| 1.018 | Br | Br | H | H | H | $n_D^{25}$ 1.5655 |
| 1.019 | Br | H | H | H | H | |
| 1.020 | Cl | H | H | H | H | |
| 1.021 | Br | H | H | $CH_3$ | H | $n_D^{25}$ 1.5360 |
| 1.022 | Cl | Cl | H | $C_2H_5$ | H | |
| 1.023 | H | Cl | –⟨phenyl⟩ | H | H | m.p. 156–159° C. |
| 1.024 | H | Cl | –⟨phenyl⟩-Cl | H | H | |

TABLE 1-continued
Compounds of formula Ia

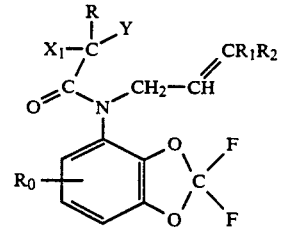

| Comp. No. | X | Y | R | R1 | R2 | phys.-chem. data |
|---|---|---|---|---|---|---|
| 1.025 | H | H | phenyl | H | H | |
| 1.026 | H | H | phenyl | CH$_3$ | H | |
| 1.027 | H | Br | phenyl | CH$_3$ | H | |
| 1.028 | Cl | Cl | 3-F-phenyl | H | H | |
| 1.029 | Cl | Cl | CH$_3$ | H | H | $n_D^{26}$ 1.5275 |
| 1.030 | F | Cl | CH$_3$ | H | H | |
| 1.031 | Cl | H | CH$_3$ | H | H | |
| 1.032 | Cl | Cl | CH$_3$ | CH$_3$ | H | |
| 1.033 | Cl | Cl | C$_2$H$_5$ | H | H | |
| 1.034 | Cl | H | CH$_3$ | CH$_3$ | H | |
| 1.035 | F | H | H | H | H | $n_D^{25}$ 1.5020 |
| 1.036 | Cl | Cl | H | H | H | m.p. 84–85° C. (E-isomer) |
| 1.037 | Cl | Cl | H | H | H | m.p. 65–66° C. (Z-isomer) |
| 1.038 | H | H | H | H | CH$_3$ | $n_D^{23}$ 1.5040 |
| 1.039 | Br | Br | H | H | CH$_3$ | $n_D^{25}$ 1.5502 |
| 1.040 | F | Cl | F | H | CH$_3$ | m.p. 84–88° C. (diastereomer B) |
| 1.041 | F | Cl | F | H | CH$_3$ | oil (diastereomer A) |
| 1.042 | F | H | F | H | CH$_3$ | m.p. 63–64° C. |
| 1.043 | F | Cl | F | H | H | m.p. 83–85° C. |

TABLE 2
Compounds of formula Ib

| Comp. No. | X | Y | R$_0$ | R | R$_1$ | R$_2$ | phys.-chem. data |
|---|---|---|---|---|---|---|---|
| 2.001 | Cl | Cl | 5-Cl | H | H | H | |
| 2.002 | Cl | Cl | 5-Cl | H | CH$_3$ | H | |
| 2.003 | Cl | H | 5-Cl | H | CH$_3$ | H | |
| 2.004 | F | Cl | 5-Cl | H | H | H | |
| 2.005 | F | H | 5-Cl | H | CH$_3$ | H | |
| 2.006 | Cl | Cl | 6-Cl | H | H | H | |
| 2.007 | Cl | Cl | 6-Cl | H | CH$_3$ | H | |
| 2.008 | Cl | H | 6-Cl | H | CH$_3$ | H | |
| 2.009 | F | H | 6-Cl | H | CH$_3$ | H | |
| 2.010 | F | Cl | 6-Cl | H | H | H | |
| 2.011 | Cl | Cl | 5-Br | H | H | H | |
| 2.012 | F | Cl | 5-Br | H | H | H | |

TABLE 3
Compounds of formula II

| Comp. No. | X$_1$ | Y | R$_0$ | R | R$_1$ | R$_2$ | phys.-chem. data |
|---|---|---|---|---|---|---|---|
| 3.001 | Cl | Cl | H | H | H | H | $n_D^{25}$ 1.5120 |
| 3.002 | Cl | Cl | H | H | CH$_3$ | H | $n_D^{25}$ 1.5117 |
| 3.003 | F | Cl | H | H | H | H | $n_D^{25}$ 1.4940 |
| 3.004 | F | Cl | H | H | CH$_3$ | H | $n_D^{25}$ 1.4922 |
| 3.005 | Cl | Cl | H | H | CH$_3$ | CH$_3$ | $n_D^{25}$ 1.5120 |
| 3.006 | F | Cl | H | H | CH$_3$ | CH$_3$ | $n_D^{25}$ 1.4960 |
| 3.007 | Cl | Cl | H | Cl | H | H | $n_D^{25}$ 1.5182 |
| 3.008 | Cl | Cl | H | Cl | CH$_3$ | H | |
| 3.009 | F | Cl | H | Cl | H | H | |
| 3.010 | F | Cl | H | Cl | CH$_3$ | H | |
| 3.011 | Br | Br | H | H | H | H | $n_D^{25}$ 1.5383 |
| 3.012 | Cl | Cl | H | H | C$_2$H$_5$ | H | |
| 3.013 | H | Cl | H | phenyl | H | H | $n_D^{25}$ 1.5435 |
| 3.014 | H | Cl | H | 3-Cl-phenyl | H | H | |
| 3.015 | H | Br | H | phenyl | CH$_3$ | H | |
| 3.016 | Cl | Cl | H | 3-F-phenyl | H | H | |
| 3.017 | Cl | Cl | H | CH$_3$ | H | H | $n_D^{25}$ 1.5015 |
| 3.018 | Cl | Cl | H | C$_2$H$_5$ | H | H | |
| 3.019 | Cl | Cl | 5-Cl | H | H | H | |
| 3.020 | Cl | Cl | 5-Cl | H | CH$_3$ | H | |
| 3.021 | F | Cl | 5-Cl | H | H | H | |
| 3.022 | Cl | Cl | 6-Cl | H | H | H | |
| 3.023 | Cl | Cl | 6-Cl | H | CH$_3$ | H | |
| 3.024 | F | Cl | 6-Cl | H | CH$_3$ | H | |
| 3.025 | F | Cl | 6-Cl | H | H | H | |
| 3.026 | Cl | Cl | 5-Br | H | H | H | |
| 3.027 | F | Cl | 5-Br | H | H | H | |
| 3.028 | F | Cl | H | F | CH$_3$ | H | $n_D^{25}$ 1.4735 |
| 3.029 | F | Cl | H | F | H | H | $n_D^{25}$ 1.4716 |

TABLE 3-continued

Compounds of formula II $$X_1-\underset{\underset{\underset{O=C}{|}}{|}}{\overset{R}{C}}\overset{Y}{\diagdown}\overset{CR_1R_2}{\diagup}$$
(with N-CH_2-CH group attached to phenyl bearing R_0 and the dioxole-CF_2 ring)

| Comp. No. | $X_1$ | Y | $R_0$ | R | $R_1$ | $R_2$ | phys.-chem. data |
|---|---|---|---|---|---|---|---|
| 3.030 | Br | Br | H | H | $CH_3$ | H | $n_D^{25}$ 1.5383 |

2. Formulation Examples for compounds of formula I
(throughout, percentages are by weight)

| F1. Wettable powders | a) | b) | c) |
|---|---|---|---|
| Compound of Tables 1 and 2 | 20% | 50% | 0.5% |
| sodium lignosulfonate | 5% | 5% | 5% |
| sodium lauryl sulfate | 3% | — | — |
| sodium diisobutylnaphthalene-sulfonate | — | 6% | 6% |
| octylphenolpolyethylene glycol ether (7–8 mol of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| F2. Emulsifiable concentrates | a) | b) |
|---|---|---|
| Compound of Tables 1 and 2 | 10% | 1% |
| calcium dodecylbenzenesulfonate | 3% | 3% |
| octylphenolpolyethylene glycol ether (4–5 mol of ethylene oxide) | 3% | 3% |
| castor oil polyethylene glycol ether (36 mol of ethylene oxide) | 4% | 4% |
| cyclohexanone | 30% | 10% |
| xylene mixture | 50% | 79% |

Emulsions of any required concentration can be obtained from such concentrates by dilution with water.

| F3. Dusts | a) | b) |
|---|---|---|
| Compound of Tables 1 and 2 | 0.1% | 1% |
| talcum | 99.9% | — |
| kaolin | — | 99% |

Ready-for-use dusts are obtained by intimately mixing the carriers with the active ingredient.

| F4. Extruder granules | a) | b) |
|---|---|---|
| Compound of Tables 1 and 2 | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is moistened with water. The mixture is extruded and then dried in a stream of air.

| F5. Coated granules | |
|---|---|
| Compound of Tables 1 and 2 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| F6. Suspension concentrate | a) | b) |
|---|---|---|
| Compound of Tables 1 and 2 | 5% | 40% |
| ethylene glycol | 10% | 10% |
| nonylphenolpolyethylene glycol ether (15 mol of ethylene oxide) | 1% | 6% |
| sodium lignosulfonate | 5% | 10% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 77% | 32% |

The finely ground active ingredient is intimately mixed with the adjuvants, giving a suspension concentrate from which suspensions of any desired concentration can be obtained by dilution with water.

| F7. Salt solution | |
|---|---|
| Compound of Tables 1 and 2 | 5% |
| isopropylamine | 1% |
| octylphenolpolyethylene glycol ether (78 mol of ethylene oxide) | 91% |

The rates of application are generally from 0.005 to 4 kg per hectare, preferably from 0.01 to 2 kg per hectare.

3. biological Examples

EXAMPLE B1

Description of test for preemergence herbicidal action

Monocotyledonous and dicotyledonous test plants are sown in plastic pots containing standard soil. Immediately after sowing the pots are sprayed with aqueous suspensions of the test compounds prepared from an emulsifiable concentrate (Example F2) at a rate corresponding to 4 kg and 2 kg of active ingredient per hectare (500 l water/ha). The test plants are then cultivated in a greenhouse under optimum conditions. After a period of 3 weeks the test is evaluated and the action is assessed in accordance with the following scale of nine ratings (1=total damage, 9=no action).

1:plant has not germinated or has died completely
2–3:very pronounced action
4–6:moderate action
7–8:slight action
9:no action (as untreated control)

Test plants: Avena, Setaria, Sinapis, Stellaria

TABLE 4

| | Pre-emergence action | | | |
|---|---|---|---|---|
| Comp. No. | Rate [kg a.i./ha] | Avena | Setaria | Sinapis | Stellaria |
| 1.001 | 4 | 1 | 1 | 1 | 1 |
| 1.004 | 2 | 6 | 1 | 1 | 2 |
| 1.006 | 2 | 1 | 1 | 1 | 1 |
| 1.011 | 2 | 6 | 1 | 1 | 1 |
| 1.021 | 2 | 1 | 1 | 1 | 1 |

TABLE 4-continued

| Comp. No. | Rate [kg a.i./ha] | Avena | Setaria | Sinapis | Stellaria |
|---|---|---|---|---|---|
| 1.035 | 2 | 7 | 1 | 1 | 1 |
| 1.036 | 2 | 1 | 1 | 1 | 1 |
| 1.038 | 2 | 7 | 1 | 1 | 2 |
| 1.042 | 2 | 1 | 1 | 1 | 1 |

The same results are obtained when the compounds of formula I are formulated in accordance with Examples F1 and F3 to F7.

EXAMPLE B2

Description of test for herbicidal action in water rice ("paddy")

The test plants are sown on the surface of standard soil in plastic pots which are then filled with water to the surface of the soil. 3 days later aqueous suspensions of the test compounds prepared from an emulsifiable concentrate (Example F2) are applied to the test plants at a rate corresponding to 4 kg and 2 kg of active ingredient per hectare (500 l water/ha). Immediately after application the water level is increased by 1 cm and the test plants are grown in a greenhouse under optimum conditions. Two weeks after application the test is evaluated using a scale of nine ratings (1=total damage, 9=no action). Ratings from 1 to 4 (especially 1 to 3) denote good to very good herbicidal activity.
Test plant: Echinochloa In this test a rating of 1 is achieved with compound number 1.001.

The same results are obtained when the compounds of formula I are formulated in accordance with Examples F1 and F3 to F7.

What is claimed is:

1. A compound of formula I

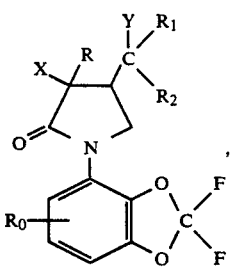
(I)

wherein
R is hydrogen, $C_1$-$C_4$alkyl, or phenyl unsubstituted or substituted by halogen, $C_1$-$C_4$alkyl or by $C_1$-$C_4$-haloalkyl, or is fluorine, chlorine or bromine;
$R_0$ is hydrogen or halogen;
$R_1$ and $R_2$ independently of one another are hydrogen or $C_1$-$C_4$alkyl;
X is hydrogen, fluorine, chlorine, bromine, cyano, —$COOR_1$, —$CONR_1R_2$, —$NH_2$ or —$NHCOR_3$, wherein $R_1$ and $R_2$ are as defined, and $R_3$ is $C_1$-$C_4$alkyl; and
Y is hydrogen, chlorine or bromine; or a diastereoisomeric form thereof.

2. A compound according to claim 1 of formula $I_a$

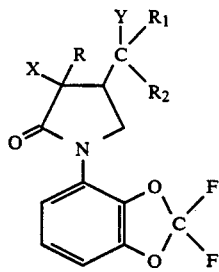
($I_a$)

wherein R, $R_1$, $R_2$, X and Y are as defined in claim 1.

3. A compound according to claim 2, wherein
R is hydrogen, methyl, fluorine, chlorine, phenyl, 3-chlorophenyl or or 3fluorophenyl;
$R_1$ and $R_2$ independently of one another are hydrogen, methyl or ethyl; and
X is hydrogen, fluorine, chlorine or bromine.

4. A compound according to claim 2,
wherein
R is hydrogen or phenyl;
$R_1$ and $R_2$ independently of one another are hydrogen or methyl;
X is hydrogen, fluorine or chlorine; and
Y is hydrogen or chlorine.

5. A compound according to claim 1 of formula $I_b$

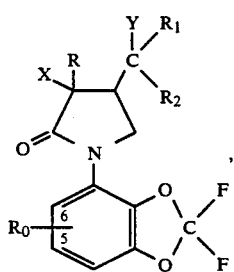
($I_b$)

wherein
$R_0$ is bonded in the 5- or 6-position and is halogen, especially chlorine or bromine;
R is hydrogen, methyl or ethyl;
$R_1$ and $R_2$ independently of one another are hydrogen or methyl;
X is fluorine or chlorine; and
Y is hydrogen or chlorine.

6. A compound according to claim 1,
wherein
R is hydrogen, fluorine, chlorine, methyl, ethyl, phenyl, 3-chlorophenyl or 3-fluorophenyl;
$R_0$ is hydrogen, 5- or 6-chlorine, or 5-bromine;
$R_1$ and $R_2$ independently of one another are hydrogen, methyl or ethyl; and
X is hydrogen, fluorine, chlorine or bromine.

7. A compound according to claim 6,
wherein
R is hydrogen, fluorine, chlorine, methyl or phenyl;
$R_0$ is hydrogen; and
$R_1$ and $R_2$ independently of one another are hydrogen or methyl.

8. A compound according to claim 1, selected from the group:
N-[(2,3-difluoromethylenedioxy)-phenyl]-3-chloro-4-chloromethylpyrrolidin-2-one;
N-[(2,3-difluoromethylenedioxy)-phenyl]-3-fluoro-4-ethylpyrrolidin-2-one;

N-[(2,3-difluoromethylenedioxy)-phenyl]-3,3-dichloro-4-chloromethylpyrrolidin-2-one;

N-[(2,3-difluoromethylenedioxy)-phenyl]-3-bromo-4-ethylpyrrolidin-2-one; and

N-[(2,3-difluoromethylenedioxy)-phenyl]-3,3-difluoro-4-ethylpyrrolidin-2-one.

9. A herbicidal composition which comprises a herbicidally effective amount of a compound of formula I according to claim 1 and a carrier.

10. A composition according to claim 9, which comprises from 0.1 to 95% of a compound of formula I, from 1 to 99% of a solid or liquid adjuvant and from 0 to 25%, especially from 0.1 to 25%, of a surfactant.

11. A method of controlling undesired plant growth, which comprises applying an effective amount of a compound of formula I according to claim 1, or of a composition comprising that compound, to the plants or to the locus thereof.

12. A method according to claim 11, which comprises applying a compound of formula I at a rate of from 0.01 to 2 kg per hectare.

13. A method according to claim 11 for the selective pre- or post-emergence control of weeds in crops of useful plants.

14. A method according to claim 13, for the selective pre- or post-emergence control of weeds in crops of useful plants selected from cereals, rice, maize, soybeans and cotton.

* * * * *